(12) United States Patent
Alemany et al.

(10) Patent No.: US 6,203,810 B1
(45) Date of Patent: *Mar. 20, 2001

(54) BREATHABLE PERSPIRATION PADS HAVING ODOR CONTROL

(75) Inventors: Miguel Alemany, Montesilvano (IT); Christiane Keirat, Wolfenbuttel (DE)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/194,669

(22) PCT Filed: May 29, 1997

(86) PCT No.: PCT/US97/10227

§ 371 Date: Nov. 30, 1998

§ 102(e) Date: Nov. 30, 1998

(87) PCT Pub. No.: WO97/45013

PCT Pub. Date: Dec. 4, 1997

(30) Foreign Application Priority Data

May 31, 1996 (DE) .............................................. 296 09 657
Oct. 29, 1996 (EP) .................................................. 96117312

(51) Int. Cl.⁷ ............................ A61F 13/15; A61F 13/16; A01N 25/34; A41B 13/02

(52) U.S. Cl. .......................... 424/404; 424/400; 424/401; 602/43; 602/58; 128/287; 428/284; 428/286; 428/290; 428/297; 428/298; 428/340; 604/366; 604/378

(58) Field of Search ...................... 424/400, 401, 424/404; 602/43, 58; 128/287; 428/284, 286, 290, 297, 298, 340; 604/366, 378

(56) References Cited

U.S. PATENT DOCUMENTS

| | | | |
|---|---|---|---|
| 3,881,489 | * 5/1975 | Hartwell | 128/287 |
| 4,363,322 | 12/1982 | Anderson | 128/290 |
| 4,545,080 | * 10/1985 | Gorham | 2/54 |
| 4,856,111 | 8/1989 | Sholes | 2/56 |
| 5,037,412 | 8/1991 | Tanzer et al. | 604/359 |
| 5,079,004 | 1/1992 | Blank et al. | 424/404 |
| 5,603,653 | 2/1997 | Hartman | 450/56 |

FOREIGN PATENT DOCUMENTS

96/13991  5/1996  (WO) ............................ A41D/27/13

\* cited by examiner

*Primary Examiner*—Jos' G. Dees
*Assistant Examiner*—Kathryne E. Shelborne
(74) *Attorney, Agent, or Firm*—Joan B. Tucker

(57) ABSTRACT

The present invention relates to breathable perspiration pads such as underarm-, wrist- and head-perspiration pads, collar inserts, and shoe inserts, having a breathable backsheet, and an odor control system. The combination of breathability and the odor control system delivers an improved odor control performance of the perspiration pad.

12 Claims, No Drawings

BREATHABLE PERSPIRATION PADS HAVING ODOR CONTROL

FIELD OF THE INVENTION

The present invention relates to absorptive articles for the absorption of perspiration such as underarm perspiration pads, collar inserts, shoe inserts and the like which have an improved odour control system. The present invention both hinders the generation of perspiration and its associated malodour and effectively absorbs any perspiration produced and prevents its visible and olfactory detection.

BACKGROUND OF THE INVENTION

The generation of perspiration by the human body is a well known bodily function which is due mainly to climatic changes and physical exertion. In this manner the body provides a natural cooling system. Although the degree of perspiration generated varies from person to person, under certain circumstances the human body will always perspire. However, whilst perspiration is a natural bodily function, it is also often associated with a lack of bodily hygiene and cleanliness. In addition, the majority of people also experience discomfort whilst perspiring.

In addition, perspiration is typically also associated with the staining of clothing, which is unsightly. This problem is exacerbated by certain types of design of clothing such as tight fitting clothing and the use of synthetic materials in clothing manufacture. Unfortunately, this type of perspiration related staining of clothing is difficult to remove and often remains visible on clothing after washing or dry cleaning.

Furthermore, another problem related to the generation of perspiration is the associated and distinctive unpleasant odour. Malodorous compounds typically present, may originate from a number of sources. Firstly, the actual components of the fluid discharge i.e., perspiration may contain malodorous compounds. Secondly, malodorous compounds are also generated as a result of the degradation of the components of perspiration.

The presence and particularly the detection of perspiration is the cause of considerable embarrassment to many people, especially those people suffering from a tendency to perspire heavily. Hence, it is highly desirable to prevent the detection of human perspiration.

One means of addressing this problem is the use of antiperspirants or deodorisers which are applied to the skin in the form of aerosols, roll-ons, sticks and gels. For example EPO 710 812 discloses a method of preventing underarm malodour associated with human perspiration by the use of a macroporous crosslinked copolymer containing acrylate or methacrylate units. The polymer entraps the fatty acid components of perspiration and thereby denies access to the acid by skin bacteria and consequently reduces body malodour.

However, for many people antiperspirants and deodorants are not particularly effective. Furthermore, there is a desire of many consumers to avoid the use of such compounds on the skin as many of these compounds are considered as skin irritants and also as it is not considered to thereby hinder the body's natural reaction to perspire. In addition, such products also do not address the problem of staining of clothing. In fact, many antiperspirant products cause additional staining of clothing and contribute to the degradation of the clothing itself.

An alternative means of addressing the problem of the generation of perspiration is to use absorbent articles. Such articles have been long recognized as a means of addressing this problem and there are a number of reference to articles designed specifically to absorb perspiration, particularly designed for utilisation on areas of the body susceptible to perspiration such as the armpit, neck or soles of the feet. For example the perspiration pads as described in U.S. Pat. No. 467,898, DE 31 04 047, DE 28 41 365 and DE 39 09 218.

The primary focus of such perspiration pads is to absorb and retain fluids. This is typically achieved by providing a pad having an absorbent material and a liquid impervious backing material. In this manner the pad absorbs the excreted fluids, prevents the staining of clothing and provides wearer comfort by improving the dryness of the surface of the skin, where perspiration occurs. Another important area of development in this field is also the control of odorous compounds contained within the pads during their use.

There are numerous disclosures in the art, particularly in the field of sanitary napkins, which describe various compounds which provide odour control for use in absorbent articles. These odour control agents typically function by physical absorption of the odorous compound or by chemical interaction with the odorous compounds or their precursors or by masking the odour for example by the use of perfumes.

The use of odour control agents specifically in perspiration pads has also been in the art. For example EPO 333 773 discloses an antiperspirant pad with an absorbent layer, a thin water impervious layer having an attachment means for attachment to garments, wherein the absorbent layer contains microencapsulated actives.

Also DE 33 39 474 discloses anti-perspiration underarm pads having attachments means to garments which are also easily removed from garments comprising an absorbent material and a perfume carrier or active which terminates bacteria or microbes and is preferably encapsulated.

DE 26 17 545 discloses underarm perspiration pads comprising a coverlayer and a lower layer, the lower layer having garment attachment means. In addition the pad may contain antibacterial agents or perfume.

However, the above described odour control agents all have associated drawbacks. Many odour control agents do not provide effective odour control over a range of odours and are not effective against odours generated from perspiration.

Disposable garment shield for prevention of garment soiling and combating perspiration related odours has been disclosed in U.S. Pat. No. 5,103,500. The shield comprises a laminated body having a layer of non absorbent polymer which has adhesive attaching material, a moisture absorbing layer and a dry deodorant mixture activated by perspiration.

However, there still exists a need to provide alternative odour controlling agents or systems for effective utilization in perspiration pads. In particular, there exists a need to provide an odour control agent or system for the prevention of the detection of malodorous compounds within pads by addressing the source of the formation of the odour.

It has now been surprisingly found that the combination of a perspiration pad having a breathable backsheet together with an odour control system provides an unexpected improvement in the odour control performance of the odour control system.

The incorporation of breathable backsheets in absorbent articles such as sanitary napkins for improved wearer comfort has been described in the art such as for example in GB 2 184 389, U.S. Pat. No. 3,881,489 and EPO 203 821. U.S. Pat. No. 4,059,114 discloses the incorporation of antimicrobial agents in sanitary napkins which have vapour permeable backsheets. However, none of these prior art documents recognise the benefits of the combination of a breathable backsheet with an odour control system in perspiration pads.

It is believed that the synergic odour control performance benefit of a breathable perspiration pad in combination with an odour control agent is due to a number of factors.

Firstly, the breathability of the pad results in increased movement of the volatile malodorous compounds. Hence, the amount of actual physical contact between these compounds and the odour control agents increases. Contact between the odour control agents and the malodorous compounds is usually required in order to effectively combat the odorous compound. Frequently, large quantities of the odour control system is required within the perspiration pad order to ensure its effectiveness. This is because the odour control agents do not necessarily contact all the malodorous compounds present. Hence the cost of these products increases, so it is desirable to avoid the necessity of large quantities of the odour control system. In the present invention, the effectiveness of the odour control agent is significantly increased and thus the full capacity of the odour control agent can be utilised and hence less may be required.

Secondly, the breathability of the absorbent pad reduces the hot humid and anaerobic environment between the skin of the wearer and the surface of the perspiration pad. This hinders the growth of microorganisms, which are also known to be responsible for the generation of odorous compounds. Thus, the amount of odours associated with the presence of microorganisms is reduced by the perspiration pads of the present invention.

Thirdly, the reduction in the hot, humid and occlusive environment between the vicinity of the skin of the wearer and the wearer facing surface of the perspiration pad itself also reduces the tendency of the wearer of the product to perspire. Consequently, the amount of associated perspiration related odour will be reduced. Thus, the breathability of the pad actually reduces the amount of odour generated within the perspiration pad. As a result the odour control system works more effectively on the remaining odorous compounds present in the article.

In addition, due to the breathable nature of the pad, the malodorous compounds contained therein may, similar to water vapour and air, be more readily exchanged with the environment. Hence, malodorous compounds are able to escape from the article and are dissipated into the surroundings. More importantly, the breathability of the pad also allows the precursors compounds of malodorous compounds present in the article to escape from the perspiration pad before degradation commences and hence before malodour formation takes place.

A further advantage of the perspiration pads of the present invention is that the need to use antiperspiration products is eliminated thereby allowing the body to perspire naturally without the possibility of the generation of stains on clothing or detection of malodours.

SUMMARY OF THE INVENTION

The present invention relates to an absorbent perspiration pad, comprising an absorbent core and a backsheet, wherein said backsheet is breathable and wherein said perspiration pad further comprises an odour control system. The combination of the odour control system and the breathability of the perspiration pad provides an unexpected improvement of the odour control system performance whereby the detection of malodours and the staining of clothing is prevented.

DETAILED DESCRIPTION OF THE INVENTION

The present invention relates to breathable perspiration pads, which may be used in conjunction with articles of clothing and undergarments, or as a separate article, positioned where perspiration or excessive perspiration occurs. Examples of perspiration pads include underarm-, wrist- and head perspiration pads, collar inserts, shoe inserts, hat bands and breast pads. Typically such products comprise an absorbent core and a backsheet. According to the present invention the breathability of the perspiration pad is provided by the presence of a breathable backsheet which thereby allows the circulation of water vapour and preferably both water vapour and air through it. According to the present invention the pad further comprises an odour control system. It has now been found that a synergy exists between the breathability of the perspiration pads and the odour control system which results in an unexpected improvement of the performance of the odour control system.

Odour Control System

According to the present invention the pads comprise as an essential component an odour control system. It has been found that this combination of a breathable pad with an odour control system results in an unexpected increase in the effectiveness of the odour control system.

Any odour control agent or combinations thereof, known in the art for this purpose may be used herein as an odour control system. The art is replete with descriptions of various odour controlling agents for use in absorbent article in order to address the problem of malodour formation which may all be usefully employed in the present invention. These agents can typically be classified according to the type of odour the agent is intended to combat. Odours may be chemically classified as being acidic, basic or neutral. Acidic odour controlling agents have a pH greater than 7 and typically include sodium carbonates, sodium bicarbonates, sodium phosphates, particularly zinc and copper sulphates. Basic odour controlling agents have a pH of less than 7 and include compounds such as carboxylic acids such as citric acid, laric acid, boric acid, adipic acid and maleic acid.

Neutral odour controlling agents have a pH of approximately 7. Examples of these types of compounds include activated carbons, clays, zeolites, silicas, absorbent gelling materials, (AGM) and starches. Neutral odour control agents and systems are disclosed for example in EPO 348 978, EPO 510 619, WO 91/12029, WO 91/11977, WO 91/12030, WO 81/01643 and WO 96/06589. Also cyclodextrin and derivatives thereof may be used as described in U.S. Pat. No. 5,429,628.

Alternatively, the odour control systems may be categorised with respect to the mechanism by which the malodour detection is reduced or prevented. The above odour control agents typically control odour detection by an absorptive mechanism.

Hence, odour control systems which chemically react with malodorous compounds or with compounds which produce malodorous degradation products thereby generating compounds lacking odour or having an odour acceptable to consumers may also be utilised herein. Suitable agents include chelating agents and may be selected from amino carboxylates such as for example ethylenediaminetetracetate, as described for example in U.S. Pat. No. 4,356, 190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these compounds is in part due to their exceptional ability to remove iron, copper, calcium, magnesium and manganese ions present in the absorbed fluids and their degradation products by the formation of chelates.

Another suitable odour control system for use herein comprises a buffer system, such as citric acid and sodium bicarbonate, sodium phosphate and sorbic acid buffer systems. Also, buffer systems having a pH of from 7 to 10 as described for example in WO 94/25077 may be useful herein.

An alternative odour control system utilises ion exchange resins such as those described in U.S. Pat. No. 4,289,513 and U.S. Pat. No. 3,340,875.

Masking agents or deodorants such as perfumes may also be used as odour control agents herein. Preferably these agents are used in combination with an additional odour control agent such as zeolite as described in WO 94/22500. Also so called anti perspirants such as aluminium salts for example aluminium chloridrate and aluminium sulphate and antimicrobics such as Triclosan and benzoic, propionic and sorbic acids for example may also be used as odour control agents. Such agents are described in "The Chemistry and Manufacture of Cosmetics" Vol. 3, 2 Ed. pg. 205–208, entitled "Antiperspirants and deodorants", by W. H. Mueller and R. P. Quatrale and "The Journal of Investigative Dermatology", Vol. 88, N. 3, March Suppl. 1987., entitled "Skin Microflora", by J. J. Leydon, K. D. McGinley et al.

Other suitable odour control agents are enzyme blocking agents as described in Cosm. and Toil. 95, 48, 1980, in "Non microbiological deodorising agents" by R. Osberghaus such as triethyl cytrate and odour absorbers for example zinc ricinoleate as described in Cosmesi Funzionale, pages 465–498, ED. Singerga, 1988, G. Proserpio.

The odour control system of the present invention is preferably selected from any of the above described agents or combinations thereof. Particularly preferred are the antimicrobial agents, deodorants, antiperspirant agents and mixtures thereof. Preferred odour control systems comprising absorbing agents for use herein include the following combinations i). silica, AGM and zeolites, preferably in a ratio of from 5:1:1 to 1:1:5 most preferably 3:1:1 to 1:1:3 ii) zeolites, activated carbon and AGM, iii) silica and AGM preferably in a ratio of from 5:1 to 1:5, more preferably from 3:1 to 1:3 iv) zeolites and AGM, v) silica and zeolites, preferably in a ratio of from 1:5 to 5:1, more preferably from 1:3 to 3:1 vi). chelating agents, particularly ethylenediamine-tetracetate, and vii). chelating agents in combination with an the combination of AGM and zeolite or with the combination of AGM, zeolite and activated carbon preferably at a ratio of chelant to additional agents of from 1:10 to 10:1, more preferably from 1:5 to 5:1

The odour control system may be incorporated into the article by any of the methods disclosed in the art. For example, the odour control agents may be layered on the core of the absorbent material or mixed within the fibres of the absorbent core or layered on the backsheet. The odour control system is preferably incorporated between two layers of cellulose tissue. Optionally the odour control system may be bonded between two cellulose tissue layers with for example a hot melt adhesive or any suitable bonding system. A suitable laminate for the odour control system of the present invention is available from Korma SpA, under the code name KO.054.02.002. Alternatively, the odour control system may be contained within capsules or micro capsules which are activated by for example a change in temperature, pressure or by liquid contact on the core, backsheet or both.

The odour control agents may be incorporated as a powder or a granulate within the pad. For odour control systems comprising more that one component the agents may be granulated separately and then mixed together or granulated together.

The odour control agent may be distributed homogeneously throughout the pad or any one of the layers thereof, or may be distributed substantially in the centre of the pad or substantially on the edges of the pad.

According to the present invention the amount of odour control system incorporated into the pad may be readily determined by the man skilled in the art and is to some extend dependent on the end use of the perspiration pad and bearing in mind the perspiration pad dimensions. Typically, the pad comprises from 5 $gm^{-2}$ to 400 $gm^{-2}$, more preferably from 100 $gm^{-2}$ to 300 $gm^{-2}$, most preferably from 150 $gm^{-2}$ to 250 $gm^{-2}$ basis weight of said odour control system. For example an underarm perspiration pad may comprise from 0.25 g to 5 g, preferably from 0.4 g to 3 g, most preferably from 0.5 g to 2.5 g of said odour control system.

Backsheet

According to the present invention, the perspiration pads comprise as an essential component a breathable backsheet. The primary role of the breathable backsheet is to prevent the extrudes absorbed and contained in the pad from wetting clothing that contact the absorbent pad such as jackets, shirts, blouses, dresses, pants and undergarments. In order to achieve this the backsheet typically extends across the whole of the absorbent structure and may extend into and form part of or all sideflaps, side wrapping elements or wings. In addition however, the breathable backsheet permits the transfer of water vapour and preferably both water vapour and air through it and thus allows the circulation of air into and out of the backsheet and the perspiration pad itself.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness.

Suitable single layer breathable backsheets for use herein include those described for example in GB A 2184 389, GB A 2184 390, GB A 2184 391, U.S. Pat. Nos. 4,591,523, 3,989,867, 3,156,242 and European Patent Application number 95120653.1.

Suitable dual or multi layer breathable backsheets for use herein include those exemplified in U.S. Pat. Nos. 3,881, 489, 4,341,216, 4,713,068, 4,818,600, EPO 203 821, EPO 710 471, EPO 710 472, European Patent Application numbers 95120647.3, 95120652.3, 95120653.1 and 96830097.0.

Particularly preferred are backsheets meeting the requirements as defined in European Patent Application number 96830343.8 and more preferably wherein the perspiration pads also meets the requirements as described therein.

According to the present invention the breathable backsheet comprises at least one, preferably at least two water vapour permeable layers. Suitable water vapour permeable layers include 2 dimensional, planar micro and macroporous films, monolithic films, macroscopically expanded films and formed apertured films. According to the present invention the apertures in said layer may be of any configuration, but are preferably spherical or oblong. The apertures may also be of varying dimensions. In a preferred embodiment the apertures are preferably evenly distributed across the entire surface of the layer, however layers having only certain regions of the surface having apertures is also envisioned.

2 dimensional planar films as used herein have apertures having an average diameter of from 5 micrometers to 200 micrometers. Typically, 2-dimensional planar micro porous films suitable for use herein have apertures having average diameters of from 150 micrometers to 5 micrometers, preferably from 120 micrometers to 10 micrometers, most preferably from 90 micrometers to 15 micrometers. Typical 2 dimensional planar macroporous films have apertures having average diameters of from 200 micrometers to 90 micrometers. Macroscopically expanded films and formed apertured films suitable for use herein typically have apertures having diameters from 100 micrometers to 500 micrometers. Embodiments according to the present invention wherein the backsheet comprises a macroscopically expanded film or an apertured formed film, the backsheet will typically have an open area of more than 5%, preferably from 10% to 35% of the total backsheet surface area.

Suitable 2 dimensional planar layers of the backsheet may be made of any material known in the art, but are preferably manufactured from commonly available polymeric materials. Suitable materials are for example GORE-TEX (TM) or Sympatex (TM) type materials well known in the art for their application in so-called breathable clothing. Other suitable materials include XMP-1001 of Minnesota Mining and Manufacturing Company, St. Paul, Minn., USA. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition, the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at their terminating ends. Preferably said protuberances are of a funnel shape, similar to those described in U.S. Pat. No. 3,929,135. The apertures located within the plane and the orifices located at the terminating end of protuberance themselves maybe circular or non circular, provided the cross sectional dimension or area of the orifice at the termination of the protuberance is smaller than the cross sectional dimension or area of the aperture located within the garment facing surface of the layer. Preferably said apertured preformed films are uni directional such that they have at least substantially, if not complete one directional fluid transport towards the core. Suitable macroscopically expanded films for use herein include films as described in for example in U.S. Pat. No. 637,819 and U.S. Pat. No. 4,591,523.

Suitable macroscopically expanded films for use herein include films as described in for example U.S. Pat. No. 4,637,819 and U.S. Pat. No. 4,591,523.

Suitable monolithic films include HytreL, such as Hytrel HTR-8206 and Hytrel G 3548, available from DuPont Corporation, USA, and other such materials as described in Index 93 Congress, Session 7A "Adding value to Nonwovens", J-C. Cardinal and Y. Trouilhet, DuPont de Nemours International S.A, Switzerland.

According to the present invention the backsheet may comprise in addition to said water vapour permeable layer additional backsheet layers. Said additional layers may be located on either side of said water vapour permeable layer of the backsheet. The additional layers may be of any material, such as fibrous layers such as wovens, nonwovens or additional water vapour permeable apertured films.

According to the present invention the perspiration pads may further comprise an absorbent core. The absorbent material or core which can be fluffy fibrous absorbent core comprising hydrogel particles if desired, laminated tissues with or without particulate materials including hydrogel particles. The absorbent core fibres can be any on those known in the art including cellulose fibres or polymeric fibres rendered absorbent or even non absorbent matrix fibres. Also tissues of sufficient basis weight and absorbency can be used in the absorbent core according to the present invention.

According to the present invention the perspiration pads of the present invention may further comprise a topsheet. Suitable topsheets may comprise a single layer or a multiplicity of layers. In a preferred embodiment the topsheet comprises a first layer which provides the user facing surface of the topsheet and a second layer between the first layer and the absorbent structurelcore. The topsheet provides a layer through which the liquids to be absorbed penetrate to the absorbent material. The absorbent core is thus positioned intermediate the backsheet and the topsheet.

The topsheet as a whole and hence each layer individually needs to be compliant, soft feeling, and non-irritating to the wearer's skin. It also can have elastic characteristics allowing it to be stretched in one or two directions. Typically, the topsheet extends across the whole of the absorbent structure and can extend into and form part of or all of the preferred sideflaps, side wrapping elements or wings. According to the present invention the topsheet may be formed from any of the materials available for this purpose and known in the art, such as non woven fabrics, films or combinations of both. In a preferred embodiment of the present invention at least one of the layers of the topsheet comprises a hydrophobic, liquid permeable apertured polymeric film. Preferably, the upper layer is provided by a film material having apertures which are provided to facilitate liquid transport from the wearer facing surface towards the absorbent structure, as detailed for example in U.S. Pat. Nos. 3,929,135, 4,151,240, 4,319, 868, 4,324,426, 4,343,314 and 4,591,523. A suitable commercially available topsheet for use herein is BPC 45105 CPM available from BP Chemicals.

According to the present invention the perspiration pad is constructed by joining the various elements such as topsheet, backsheet and absorbent core by any means well known in the art. For example the backsheet and/or topsheet may be joined to the absorbent core or to each other by a continuous layer of adhesive, a patterned layer of adhesive, or an array of separate lines, spirals or spots of adhesive. Alternatively, the elements may be joined by heat bonds, pressure bonds, ultra sonic bonds, dynamic mechanical bonds or any other suitable joining means known in the art and any combination thereof. Preferably the breathable backsheet is bonded to other elements of the perspiration pads so as to minimise and preferably eliminate any reduction in the vapour permeability of the backsheet.

In a preferred embodiment of the present invention, wherein the perspiration pad is used in conjunction with articles of clothing or undergarments, the pad is also provided with a garment fastening means which allows attachment of the pad to a garment during use. For example, the garment fastening means may comprise a mechanical fastener such as hook and loop fasteners such as marketed under the tradename VELCRO, snaps or holders. Alternatively, the pad may be fastened to the garment by means of garment fastening adhesive on the backsheet. The garment fastening adhesive provides a means for securing the pad to the garment and preferably a means for securing the pad when soiled, to the fold and wrap package for convenient disposal. Typically, at least a portion of the garment facing surface of the backsheet is coated with adhesive to form the garment fastening adhesive. Any adhesive or glue used in the art for such purposes can be used for the fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, N.J., 3 Sigma 3153 manufactured by 3 Sigma, LA203 available from Savare SpA, Italy and Fuller H-2238ZP manufactured by the H.B. Fuller Co.

The garment fastening adhesive is typically applied to the backsheet by slot coating. In order to reduce the effect of the adhesive on the breathability of the backsheet and perspiration pad as a whole, the adhesive is preferably applied such that at least 60%, preferably at least 80%, most preferably at least 90% of the garment facing surface of the backsheet is adhesive free. The required adhesiveness can still however be provided even when using reduced surface coverage by using particular distribution, such as thinner strips, discontinuous strips, intermittent dots, random spiral patterns or mixtures thereof.

The garment fastening adhesive is typically covered with a removable release paper or film in order to prevent the adhesive from drying out or adhering to another surface other than the garment prior to use. Any commercially available release paper or film may be used. Suitable examples include BL 40G EF MGA SILOX C4R10, BL 30MG-A SILOX EI/O and BL 30 MG-A SILOX 4 P/O available from Akrosil Corporation.

In an alternative embodiment of the present invention the perspiration pad may be provided with a wearer fastening means whereby the pad is provided with means to be attached to the body of the wearer as opposed to the garment of the wearer. Typically such wearer fastening adhesives are positioned on at least a portion of the wearer facing surface of the topsheet, if present, or the absorbent core. Alternatively, particularly for applications such as wrist- and headbands the wearer fastening means may be provided by elastising at least part of the pad.

According to the present invention the perspiration pad may find utility as underarm-, wrist- and (fore) head perspiration pads, collar inserts, shoe inserts, hat bands and breast pads. The perspiration pad may also find utility in clothing in particular sports clothing. The present invention finds particular susceptibility as underarm perspiration pads. In addition to the components described herein above, the perspiration pad may also comprise all those features and parts which are typical for products in the context of their intended use such as garment fastening means, release paper, wrapping elements and the like. Typically the dimension, flexibility, size and shape of the pad will depend on the intended location of the pad on the body and can be easily adapted by the skilled man dependent on the end use. For example underarm prosperation pads are typically provided in a circular or oval shape or in a waning circular or waning oval shape and are usually symmetrical. Similarly the perspiration pads may be provided in a range of colours in order to more effectively camouflage the use of the pads, particularly when utilised under clothing.

An example of a perspiration pad according to the present invention for utilization as an underarm sweat pat has oval dimensions of 150 mm and 100 mm and, comprises a dual apertured formed film material available from B.P. Chemicals under the code name BPC 45105 CPM as a topsheet. The topsheet is placed directly above an absorbent core odour control laminate containing absorbent gelling material and zedite as odour control actives and available from Korma SpA, Italy under the code KO.054.02.002. The backsheet comprises two layers, a first layer in direct contact with the garment facing surface of the absorbent core comprising an apertured formed film material supplied by Tredgar Film Products, B. V. under the code name S225MD25 and, a second nonwoven layer placed directly below the garment facing film available from Cororin GmbH under the code name MD 2005. All the layers are joined together by spray or spiralled application of a hot melt adhesive. The garment fastening means is an adhesive available from Savare SpA, under the code name LA203 and is applied in 5 mm strips each separated by 5 mm, to the garment facing surface of the nonwoven backsheet layer.

What is claimed is:

1. A perspiration pad comprising a backsheet and an absorbent core, characterized in that said backsheet is breathable and said perspiration pad comprises an antiperspirant and an odour control system comprising an odour control agent selected from the group consisting of acidic odour controlling agents, neutral odour controlling agents, basic odour controlling agents, antimicrobial agents, chelating agents, and mixtures thereof.

2. A perspiration pad according to claim 1, wherein said breathable backsheet comprises at least one layer of an apertured formed polymeric film, a 2-dimensional planar apertured film, or a monolithic film.

3. A perspiration pad according to claim 2, wherein said layer is a 2 dimensional planar apertured layer, wherein said apertures have an average diameter of from 150 micrometers to 5 micrometers.

4. A perspiration pad according to claim 2, wherein said layer is an apertured formed polymeric film, wherein said apertures have an average diameter of from 100 micrometers to 500 micrometers.

5. A perspiration pad according to claim 2, wherein said breathable backsheet comprises at least two layers, a first layer comprising an apertured layer and a second layer comprising a fibrous layer.

6. A perspiration pad according to claim 1, wherein said perspiration pad further comprises a topsheet and wherein said absorbent core is intermediate said topsheet and said backsheet.

7. A perspiration pad according to claim 1, wherein said pad is an underarm perspiration pad.

8. A perspiration pad according to claim 1, wherein said backsheet is provided with garment fastening means.

9. A perspiration pad according to claim 8, wherein said garment fastening means comprise garment adhesive means having at least 1 adhesive strip.

10. A perspiration pad according to claim 1, wherein said acidic odour controlling agent is selected from the group consisting of sodium carbonates, sodium bicarbonates, sodium phosphates, zinc sulphates, copper sulfates, and mixtures thereof.

11. A perspiration pad according to claim 1, wherein said neutral odour controlling agent is selected from the group consisting of activated carbons, clays, zeolites, silicas, absorbent gelling materials, starches, and mixtures thereof.

12. A perspiration pad according to claim 1, wherein said basic odour controlling agent is selected from the group consisting of citric acid, lauric acid, boric acid, adipic acid, maleic acid, and mixtures thereof.

* * * * *